United States Patent [19]

Nakamura

[11] 4,039,559
[45] Aug. 2, 1977

[54] ALIPHATIC CARBOXYLIC ACID ESTERS OF VITAMIN E AND PROCESS FOR PREPARATION THEREOF

[75] Inventor: Tetsuya Nakamura, Tokyo, Japan

[73] Assignee: Eisai Co., Ltd., Tokyo, Japan

[21] Appl. No.: 596,569

[22] Filed: July 16, 1975

[30] Foreign Application Priority Data

July 18, 1974    Japan .................................. 49-81692

[51] Int. Cl.² .......................................... C07D 311/72
[52] U.S. Cl. ................................. 260/345.5; 424/283
[58] Field of Search ..................................... 260/345.5

[56] References Cited

U.S. PATENT DOCUMENTS

| | | | |
|---|---|---|---|
| 3,455,959 | 7/1969 | Mayer et al. | 260/345.5 |
| 3,789,086 | 1/1974 | Frick et al. | 260/345.5 |
| 3,869,477 | 3/1975 | Shindo et al. | 260/345.5 |
| 3,883,565 | 5/1975 | Mulholland | 260/345.5 |

*Primary Examiner*—James O. Thomas, Jr.
*Assistant Examiner*—Nicky Chan
*Attorney, Agent, or Firm*—Blanchard, Flynn, Thiel, Boutell & Tanis

[57] ABSTRACT

Aliphatic carboxylic acid esters of Vitamin E wherein the aliphatic carboxylic acid ester moiety is branched at the α-position. The compounds exhibit the biological activities of Vitamin E for a long time.

8 Claims, 1 Drawing Figure

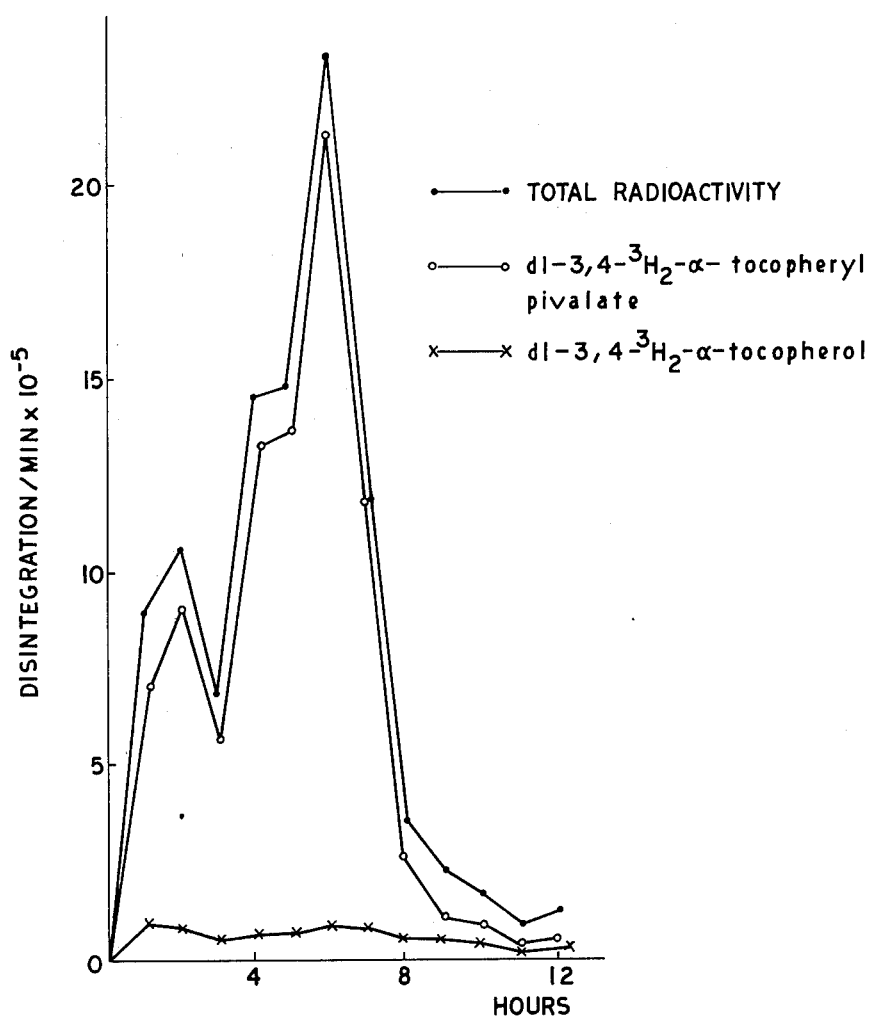

ALIPHATIC CARBOXYLIC ACID ESTERS OF VITAMIN E AND PROCESS FOR PREPARATION THEREOF

This invention relates to aliphatic carboxylic acid esters of vitamin E, namely, esters of vitamin E with aliphatic carboxylic acids having at least one branched methyl group at the α-position. More particularly, this invention relates to the compounds having the formula (I):

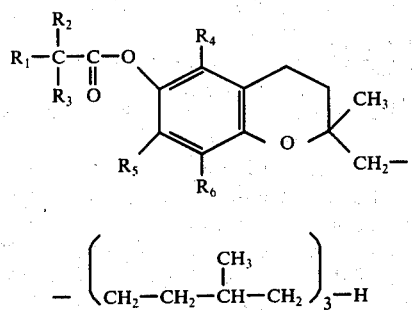

wherein $R_1$ is $CH_3-(CH_2)_n-$ in which $n$ is 0 or an integer of 1 to 4, $R_2$ and $R_3$ are hydrogen or methyl, with the proviso that at least one of $R_2$ and $R_3$ is methyl, and $R_4$, $R_5$, and $R_6$ are hydrogen or methyl, and a process for preparing the same.

As the aliphatic carboxylic acids that supply the ester moiety, there can be mentioned, for example, pivalic acid, isobutyric acid, α-methylvaleric acid, α-α-dimethylvaleric acid, α-methylcaproic acid and α,α-dimethylcaproic acid.

The term "vitamin E" referred to in the instant specification means a series of tocopherol analogues having an activity of vitamin E, such as α-Tocopherol ($R_4$, $R_5$ and $R_6$ are methyl in the above formula (I)), β-Tocopherol ($R_4$ and $R_6$ are methyl, $R_5$ is hydrogen in the above formula (I)), γ-Tocopherol ($R_4$ is hydrogen, $R_5$ and $R_6$ are methyl in the above formula (I)), δ-Tocopherol ($R_4$ and $R_5$ are hydrogen, $R_6$ is methyl in the above formula (I)) and the like.

It is a primary object of this invention to provide compounds having an activity of vitamin E and which can be more effectively utilized in the living body.

Another object of this invention is to provide a process for the preparation of such compounds having an activity of vitamin E which can be effectively utilized in the living body.

The vitamin E esters of the present invention of formula (I) can be prepared, for example, by the process described below.

Namely, the compounds (I) are prepared by reacting vitamin E with an aliphatic carboxylic acid having at least one methyl group as a branch at the α-position, which acid has the following formula:

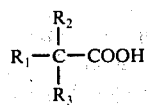

wherein $R_1$ is $CH_3-(CH_2)_n-$ in which $n$ is 0 or an integer of 1 to 4, and $R_2$ and $R_3$ are hydrogen or methyl with the proviso that at least one of $R_2$ and $R_3$ is methyl, or a reactive derivative of said aliphatic carboxylic acid.

As the reactive derivative of the carboxylic acid, there can be mentioned, for example, acid chlorides, acid anhydrides, mixed acid anhydrides and the like. When a reactive derivative is employed, the reaction is smoothly advanced by employing an organic base such as pyridine, dimethylformamide and trimethylamine, present in the reaction mixture as a solvent and also as a catalyst.

When the carboxylic acid per se is employed, it is possible to employ a conventional esterification method using a dehydration catalyst such as sulfuric acid and p-toluene-sulfonic acid and a method using a polyphosphate ester as a catalyst. If the esterification is conducted by using a polyphosphate ester as a catalyst, the reaction is advanced especially smoothly and post treatments can be greatly facilitated.

Vitamin E is highly valued as an antioxidant for the living body, and its clinical application field has recently been broadened and the demand for vitamin E has been increasing. Vitamin E is a compound having a phenolic hydroxyl group, and free vitamin E is generally unstable to oxidation. The oxidation product of vitamin E, namely tocophorylquinone, does not have the biological activity of vitamin E. Accordingly, vitamin E is frequently converted to such derivatives as tocopheryl acetate, tocopheryl hemisuccinate and tocopheryl palmitate so as to obtain vitamin E preparations having an improved storage stability. Since these esters are of acceptable stability for pharmaceutical purposes and can be handled very easily, they are effective as vitamin E preparations. In the case of oral administration, when each of these prior art vitamin E esters is absorbed through the intestinal tract of the living body, it is completely hydrolyzed by contact with pancreatic juice enzymes and intestinal enzymes and the ester is absorbed in the form of free tocopherol. In other words, when the foregoing esters are employed as sources of vitamin E in the living body, the differences between the esters actually administered disappears and each of them is converted to free tocopherol when it is absorbed in the living body.

When esters of vitamin A, which is a fat-soluble vitamin like vitamin E, are orally administered, the esters are once hydrolyzed in the intestinal tract and are then re-synthesized to higher fatty acid esters, mainly palmitate, in the intestinal mucosa. It is considered that these re-synthesized esters have a great significance for manifestation of biological activities. In order for vitamin A esters to be absorbed in the intestinal tract, it is indispensable that they should be hydrolyzed in the intestinal tract. It has heretofore been considered that vitamin E esters are absorbed in the intestinal tract along a course similar to that in the case of vitamin A. It is known that the hydrolyzed ester of vitamin E is absorbed into the circulation system in the free form upon contact with intestinal mucosa enzymes without undergoing re-synthesis. However, it has been reported that free tocopherol is readily oxidized in the living body and is converted to tocophorylquinone or other oxidation products (H. E. Gallo-Torres et al, Lipids, 6, 318 (1971)).

The vitamin E esters of Formula (I) prepared according to the process of this invention possess unique characteristics in comparison with those of known vitamin E derivatives. More specifically, it has been confirmed that the majorities of the administered amounts of the formula (I) esters are absorbed through the intestinal tract in an unchanged form and they appear and are present in lymph in their starting ester forms. The biological significance of the esters of formula (I) which are absorbed in the circulation system in the unchanged forms is that they are gradually hydrolyzed by contacts with enzymes present in various organs in the living body and release free tocopherol continuously for a long time, whereby they continuously exhibit the biological activities of vitamin E for a long time in the tissue in which they have been distributed.

Further, the formula (I) esters according to the invention can maintain the existence of the terpenoid chroman ring for a long period of time. Tocophorylquinone, which is said to be produced after vitamin E exhibits an anti-oxidation action, has no vitamin E effect and quickly disappears from the living body (O. Wiss, H. Gloor, Vitamins & Hormones 24, 575 (1966)). The formula (I) esters according to the invention which can be greatly distributed in unchanged form in the living body are more gradually or slowly converted into tocopherolquinone than is tocopherol, per se. Recently, it has been reported that the physiological effect of vitamin E is based not only on the anti-oxidation activity of the chromanol nuclei, but also upon some contribution of the terpenoid component of the terpenoid chroman to the stabilization of biomembrane (A. T. Diplock, J. A. Lucy, FEBS Letters 29, 205 (1973)). Accordingly the formula (I) esters according to the invention will greatly contribute to the stabilization of the biomembrane. An experiment was performed in which the $\beta$-glucuronidase in serum was measured by the method of Fishman et al (Methods in Enzymology 1,262) using male Wistar rats (weighing 150 to 180 g) grouped into three groups, each consisting of three rats. To the respective groups of rats, there was administered

| | |
|---|---|
| First: Group (control) | Only an emulsion composed of sodium taurocholate, monoolein and physiological saline solution was administered in an amount of 10 ml/kg, per day, for five days. |
| Second: Group (control) | In addition to the same administration of the emulsion, as for the first control group, 0.5 ml/kg of carbon tetrachloride was administered intraperitoneally immediately after the administration of the emulsion on the fifth day. |
| Third: Group | An emulsion prepared by that 28 mg/ml of dl-α-tocopheryl pivalate was added to the emulsion of the first group was administered in an amount of 10 ml/kg, per day, for five days, and then 0.5 ml/kg of carbon tetrachloride was administered intraperitoneally immediately after the administration of the emulsion on the fifth day. |

Twenty four hours after the administration of carbon tetrachloride, a blood sample was taken from the abdominal aorta of each rat held under ethyl ether anaethesia to obtain serum. Table 1 below shows the activity of $\beta$-glucuronidase in the serum obtained.

| Activity of $\beta$-glucuronidase in serum | |
|---|---|
| | $\Delta\ E_{553}$ per 0.2 ml of serum |
| First Group | 0.141 ± 0.015* |
| Second Group | 0.188 ± 0.014 |
| Third Group | 0.150 ± 0.001 |

*The figures represent average values ± S.E. (n = 3).

It will be seen that the $\beta$-glucuronidase activity is increased in the case of the group to which CCl$_4$ was administered group (second group) compared to the first group, whereas in the group to which was administered CCl$_4$ plus α-tocopheryl pivalate (third group) the $\beta$-glucuronidase activity is suppressed so to be comparable with that in the first group.

The physiological damage resulting from the administration of carbon tetrachloride to animals is thought to be due to the free radical that is brought about by the administration (Free Radical Mechanisms in Tissue Injury, T. F. Slater, pp 91, Pion Limited, London, 1972). The effect of the formula (I) esters according to the invention to suppress deterioration caused by carbon tetrachloride, which effect is recognized by taking the amount of $\beta$-glucuronidase in the serum as an index, is chiefly attributable to the stabilization of the biomembrane of the liver. The formula (I) ester according to the invention suppresses deterioration due to free radicals, i.e., it functions as a free radical scavenger, and also due to its enhanced chain reaction as a stabilizer of biomembranes. Thus, the formula (I) esters according to the invention are effective therapeutic agents for treating such diseases as liver cirrhosis, hepatic fibrosis and various other diseases that are thought to stem from the weakening of the biomembrane, for instance, diabetes mellitus, hyperlipidemia and interstitial pneumonia.

The tests of absorption of the formula (I) esters of this invention in the intestinal tract are conducted by orally administering a tritium-labeled vitamin E ester of this invention to thoracic duct-cannulated rats (J. L. Bollman et al, Journal of Laboratory & Clinical Medicine, 33, 1349–1352 (1948)), and analyzing and identifying the radioactivity that appeared in lymph. The description of the absorption test and the test results are as follows:

TEST ANIMAL

Male rats of the Wistar strain weighing 270 to 300 g were used.

EXPERIMENT APPARATUS

Bollman cage (J. L. Bollman et al, Journal of Laboratory & Clinical Medicine, 33, 1348 (1948)).

ADMINISTERED CHEMICAL AND AMOUNT ADMINISTERED

Tritium-labeled α-tocopheryl pivalate (one of the compounds of this invention) was used as the test compound.

dl-3,4-$^3$H$_2$-α-tocopheryl pivalate (590 μg, 24 μCi/rat) is formed in a mixed micelle solution comprising palmitic acid, monoolein and sodium taurocholate and the solution was administered to thoracic duct-cannulated rats by intubation. After the administration, the rats were put in the Bollman cage and only physiological saline solution was given. Lymph was collected every hour over a period of 12 hours after the administration by using a fraction collector.

MEASUREMENT METHOD

The analysis of the radioactivity manifested in the collected lymph was conducted by sampling 0.5 ml of the lymph from each of the fractions collected every hour, adding thereto 15 ml of a liquid scintillator, shaking the mixture sufficiently and measuring the total radioactivity by using a liquid scintillation counter. The analysis of the chemical form in lymph was performed by thin-layer chromatography, using silica gel GF$_{254}$. A one milliliter sample of the lymph from each of the fractions collected every hour was tested by removing proteins from the liquid sample, spotting the ethyl acetate-soluble portion to the original point of a thin layer plate of silica gel GF$_{254}$ on which were spotted several anticipated nonradioactive compounds, and developed using petroleum ether: isopropyl ether (8:2 v/v) as the developing solvent. The Rf values on the developed plate were confirmed in the dark under ultraviolet ray irradiation (wave length = 2536 A) and the thin layer was scratched out at every 1 cm zones.

The scratched layers were directly charged in a vial and 15 ml of a liquid scintillator was added. The mixture was shaken sufficiently to effect extraction. The mixture was allowed to stand still for 4 hours after the extraction, and the distribution of the radioactivity in the respective layers was determined by a liquid scintillation counter and the presence ratio of radioactivity on the developed thin layer plate was calculated.

BRIEF DESCRIPTION OF THE DRAWING

The drawing is a graph in which the ordinate indicates the radioactivity and the abscissa denotes the time after administration of the radioactive compound.

The drawing shows the results of the analysis and identification of the radioactivity manifested in lymph over a period of 12 hours when dl-3,4-$^3$H$_2$-α-tocopheryl pivalate, which is one of the compounds of this invention, was administered orally to thoracic duct-cannulated rats.

| In the drawing | (.): | total radioactivity |
|---|---|---|
| | (o): | dl-3,4-$^3$H$_2$-α-tocopheryl pivalate |
| | (x): | dl-3,4-$^3$H$_2$-α-tocopherol. |

MEASUREMENT RESULTS

The accumulated radioactivity manifested over a period of 12 hours when α-tocopheryl pivalate was administered orally to thoracic duct-cannulated rats was found to correspond to 13.5 ± 3.4 (Mean ± S.E., n = 3) of the amount administered. The absorption in lymph was at its maximum at a period about 6 hours after administration, and then, it abruptly decreased and reached substantially zero when 12 hours had passed.

As is shown in the drawing, when the chemical form of the radioactivity in the lymph was analyzed and identified over a period of 12 hours after the administration, it was found that the majority of the radioactivity analyzed each time was owing to the unchanged ester and the amount of the free tocopherol compound present in the lymph was very small. When calculated based on the values accumulated over a period of 12 hours, it was found that 86% of the total radioactivity present in the lymph was that of the unchanged ester and the radioactivity owing to the free α-tocopherol was only 9% of the total radioactivity.

This invention will now be further described by reference to the following illustrative synthesis Examples.

EXAMPLE 1 (synthesis of dl-α-tocopheryl pivalate)

Fourty three grams of dl-α-tocopherol was mixed with 11.2 g of pivalic acid and 200 g of a polyphosphate ester, (Y. Kaneoka. et. al Chem. Pharm. Bull. 13 (9) 1065–1072 (1965)) and the mixture was reacted under stirring and heating at 80° to 100° C for 4 hours. After completion of the reaction, the reaction mixture was cooled to room temperature and a dilute aqueous solution of sodium bicarbonate was added little by little to the reaction mixture liquid to neutralize it. Extraction was conducted by using hexane, and the extract was washed with water and dried with Glauber's salt. The solvent was removed by distillation under pressure to obtain a crude product as a light orange yellow viscous oil (the yield being 53.1 g). The crude product was purified by silica gel column chromatography (the developing solvent being a 9:1 or 8:2 mixed solvent of hexane:benzene). The desired product was obtained as a light yellow viscous liquid in an amount of 48.0 g (the yield being 94%).

Elementary Analysis Values as C$_{34}$H$_{58}$O$_3$: Calculated: C = 79.32%, H = 11.36%. Found: C = 79.54%, H = 11.36%.

EXAMPLE 2 (synthesis of dl-α-tocopheryl isobutyrate)

In the same manner as described in Example 1, 43.0 g of dl-α-tocopherol was reacted with 9.7 g of isobutyric acid and the reaction product was post-treated, to obtain 47.5 g (the yield being 95%) of the desired product as a light yellow viscous oil.

Elementary Analysis Values as C$_{33}$H$_{56}$O$_3$: Calculated: C = 79.14%, H = 11.27%. Found: C = 79.39%, H = 11.20%.

The embodiments of the invention in which an exclusive property or privilege is claimed are defined as follows:

1. A compound having the formula:

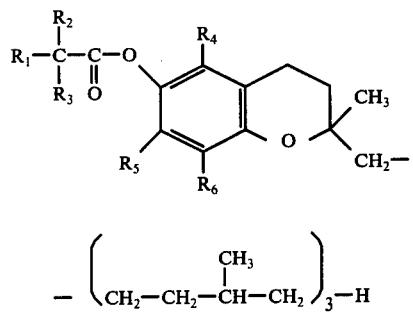

wherein R$_1$ is CH$_3$—(CH$_2$)$_n$— in which $n$ is 0 or an integer of 1 to 4, R$_2$ and R$_3$ are hydrogen or methyl with the proviso that at least one R$_2$ and R$_3$ is methyl, and R$_4$, R$_5$ and R$_6$, which can be the same or different, are hydrogen or methyl.

2. A compound as claimed in claim 1 wherein R$_4$, R$_5$ and R$_6$ are methyl.

3. A compound as claimed in claim 1 wherein R$_4$ and R$_6$ are methyl, and R$_5$ is hydrogen.

4. A compound as claimed in claim 1 wherein R$_4$ is hydrogen and R$_5$ and R$_6$ are methyl.

5. A compound as claimed in claim 1 wherein R$_4$ and R$_5$ are hydrogen and R$_6$ is methyl.

6. A compound as claimed in claim 1 wherein R$_1$, R$_2$ and R$_3$ are methyl.

7. A compound as claimed in claim 1 wherein R$_1$, R$_2$, R$_3$, R$_4$, R$_5$ and R$_6$ are methyl.

8. A compound as claimed in claim 1 wherein R$_1$, R$_2$, R$_4$, R$_5$ and R$_6$ are methyl, and R$_3$ is hydrogen.

* * * * *